United States Patent [19]

Rokugawa et al.

[11] Patent Number: 5,449,493
[45] Date of Patent: Sep. 12, 1995

[54] STIRRING DEVICE

[75] Inventors: Kyuji Rokugawa; Morito Inoue; Soichiro Sakaguchi; Hideo Oya; Noboru Aoki; Masato Saitoh, all of Tokyo, Japan

[73] Assignees: Kabushiki Kaisha Toshiba, Kawasaki; Toshiba Ceramics Co., Ltd., Tokyo, both of Japan

[21] Appl. No.: 173,934

[22] Filed: Dec. 28, 1993

Related U.S. Application Data

[63] Continuation of Ser. No. 896,384, Jun. 10, 1992, abandoned.

[30] Foreign Application Priority Data

Jun. 10, 1991 [JP] Japan .................. 3-137994

[51] Int. Cl.⁶ .............................................. B01F 11/00
[52] U.S. Cl. ..................................... 422/99; 422/224; 422/225; 366/116; 366/118; 366/120; 366/127; 310/321; 310/329
[58] Field of Search ................ 422/99, 224, 225; 366/108, 116, 118, 119, 120, 127; 310/358, 329, 321

[56] References Cited

U.S. PATENT DOCUMENTS

| 4,026,572 | 5/1977 | Yoshioka | 280/668 |
|---|---|---|---|
| 4,046,515 | 9/1977 | de Leeuw | 366/127 |
| 4,211,121 | 7/1980 | Brown | 366/116 |
| 4,373,378 | 2/1983 | Fujishiro et al. | 310/329 |
| 4,537,511 | 8/1985 | Frei | 366/127 |
| 4,550,812 | 11/1985 | Mard | 188/379 |
| 4,602,184 | 7/1986 | Meitzler | 366/118 |
| 4,612,291 | 9/1986 | Dawes | 436/174 |
| 4,778,279 | 10/1988 | Bodine | 366/118 |
| 4,780,062 | 10/1988 | Yamada et al. | 310/321 |
| 4,912,351 | 3/1990 | Takata et al. | 310/358 |

FOREIGN PATENT DOCUMENTS

| 162562 | 6/1978 | Japan . |
| 1414880 | 11/1975 | United Kingdom . |
| 871847 | 1/1979 | U.S.S.R. . |

OTHER PUBLICATIONS

Patent Abstracts of Japan, vol. 13, No. 29, (C-562)[3377]Jan. 23, 1989, & JP-A-63-232829, Sep. 28, 1988, T. Taniguchi, "Static Mixer".

*Primary Examiner*—Robert J. Warden
*Assistant Examiner*—Theresa T. Snider
*Attorney, Agent, or Firm*—Oblon, Spivak, McClelland, Maier & Neustadt

[57] ABSTRACT

Piezoelectric elements are attached to both sides of a flexible metal thin plate, thus forming a bimorph-type piezoelectric vibrator. A portion of the metal thin plate is extended to form a stirring blade. A suitable weight is attached to a part of the metal plate such that the amplitude of the blade is made greater than the amplitude of the vibrator itself. The voltage to be applied to the vibrator and the frequency are adjusted, and the vibrator is vibrated in a second-order mode. Thereby, the entire solution is moved simultaneously, vertical motion is caused, and the stirring efficiency is enhanced.

22 Claims, 12 Drawing Sheets

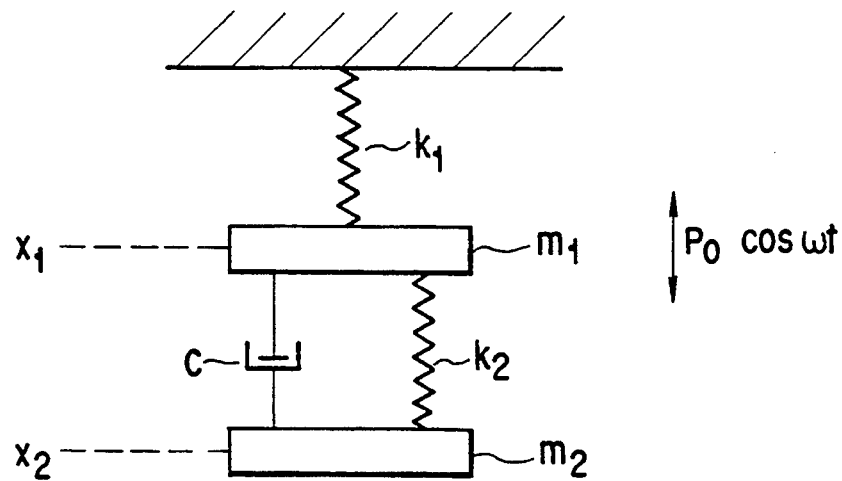
F I G. 7
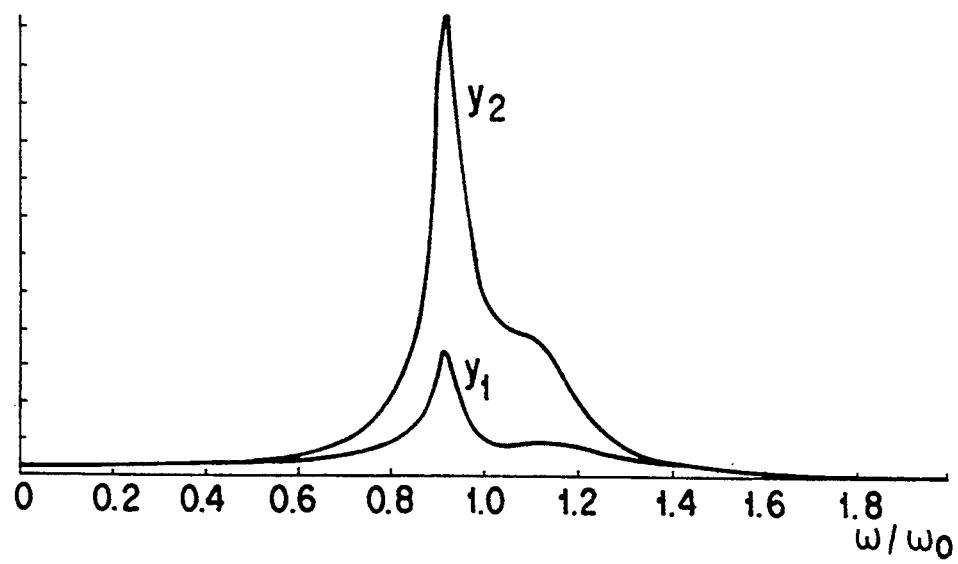
F I G. 8

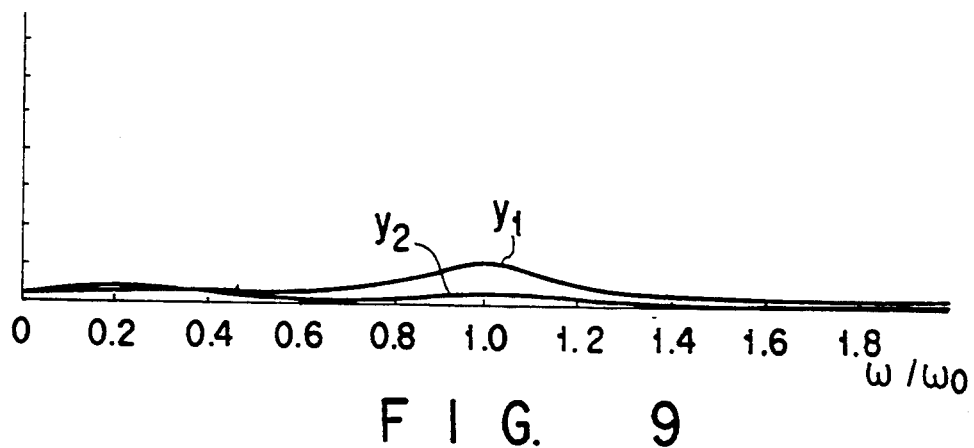
F I G. 9
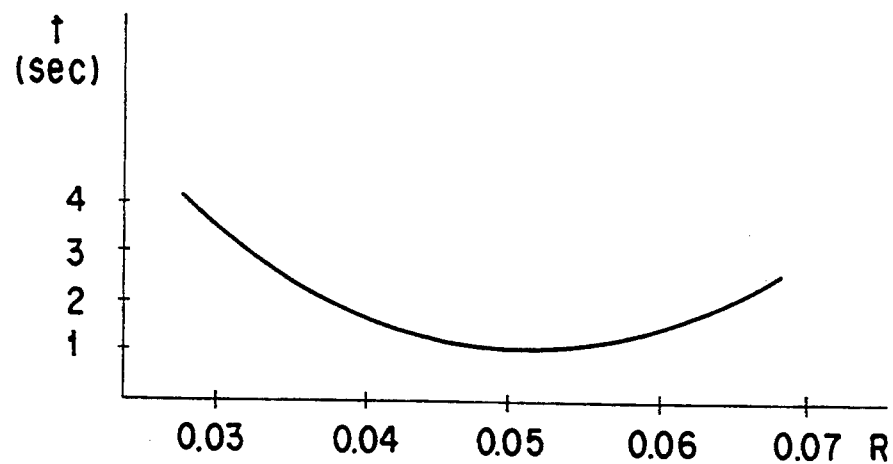
F I G. 10
F I G. 11A
(WEIGHT POSITION)
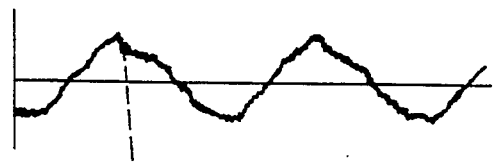
F I G. 11B
(DISTAL END)

F I G. 12A
(WEIGHT POSITION)
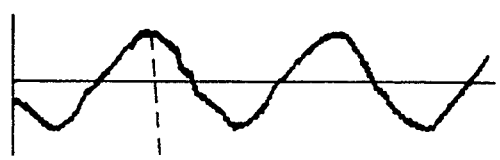
F I G. 12B
(DISTAL END)
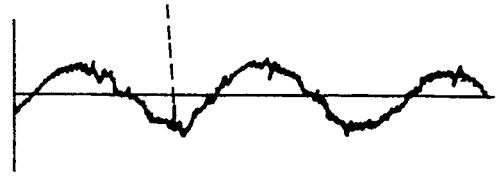
F I G. 13A
(WEIGHT POSITION)
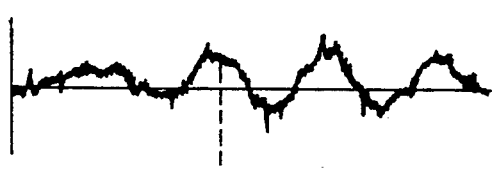
F I G. 13B
(DISTAL END)
F I G. 14A
(WEIGHT POSITION)
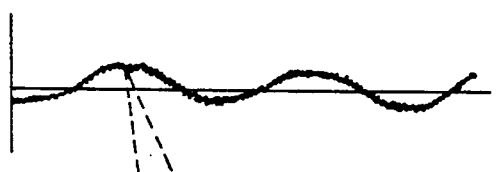
F I G. 14B
(DISTAL END)
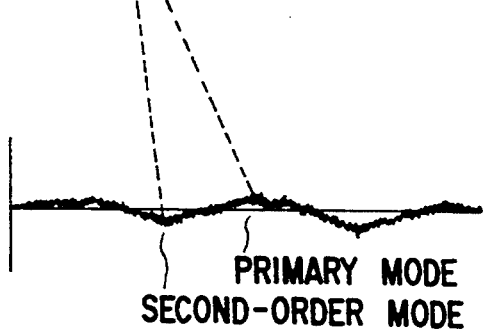
PRIMARY MODE
SECOND-ORDER MODE

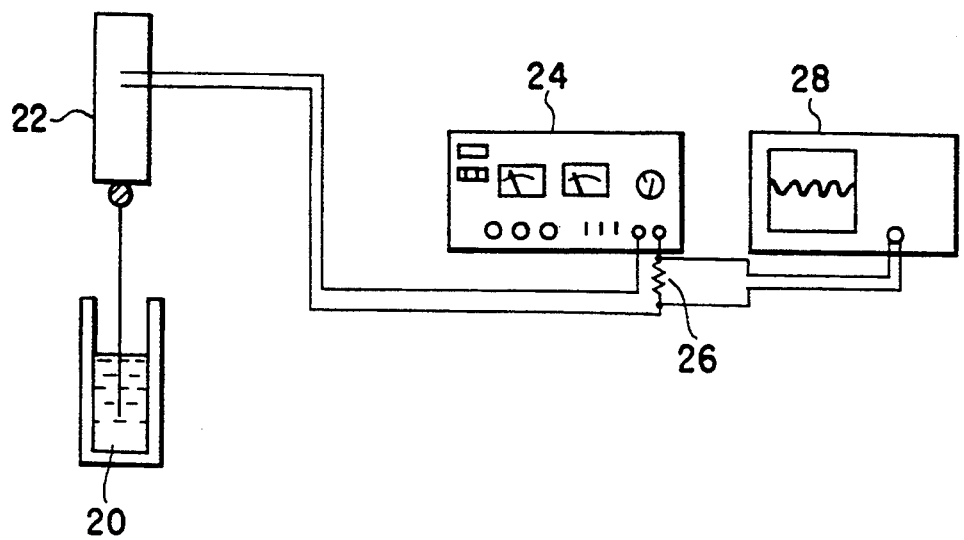
F I G. 15
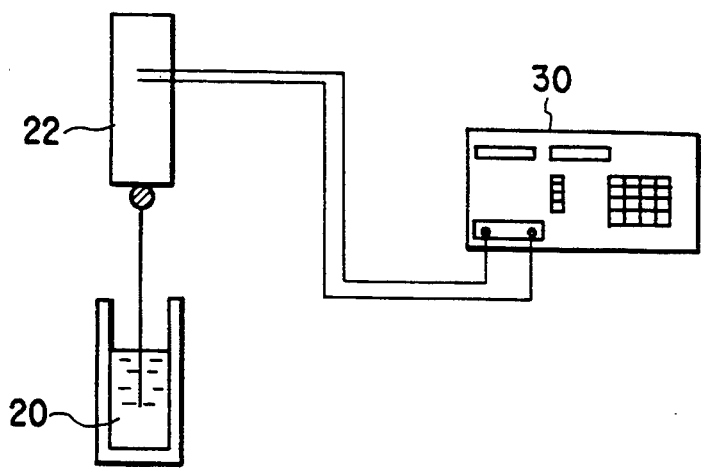
F I G. 16

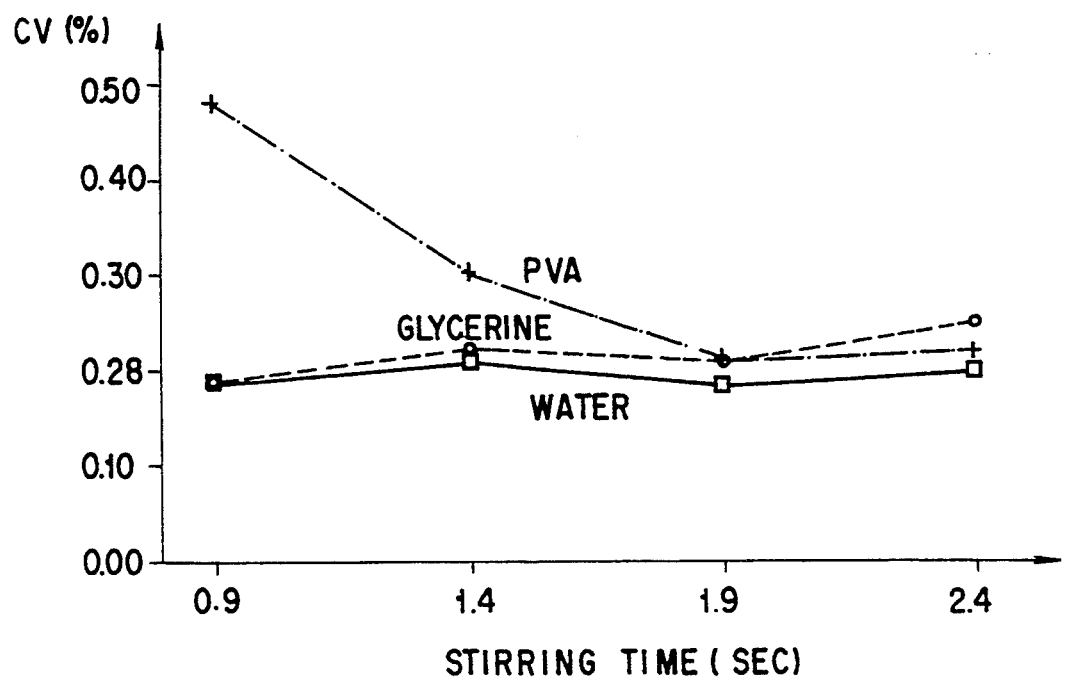
F I G. 20
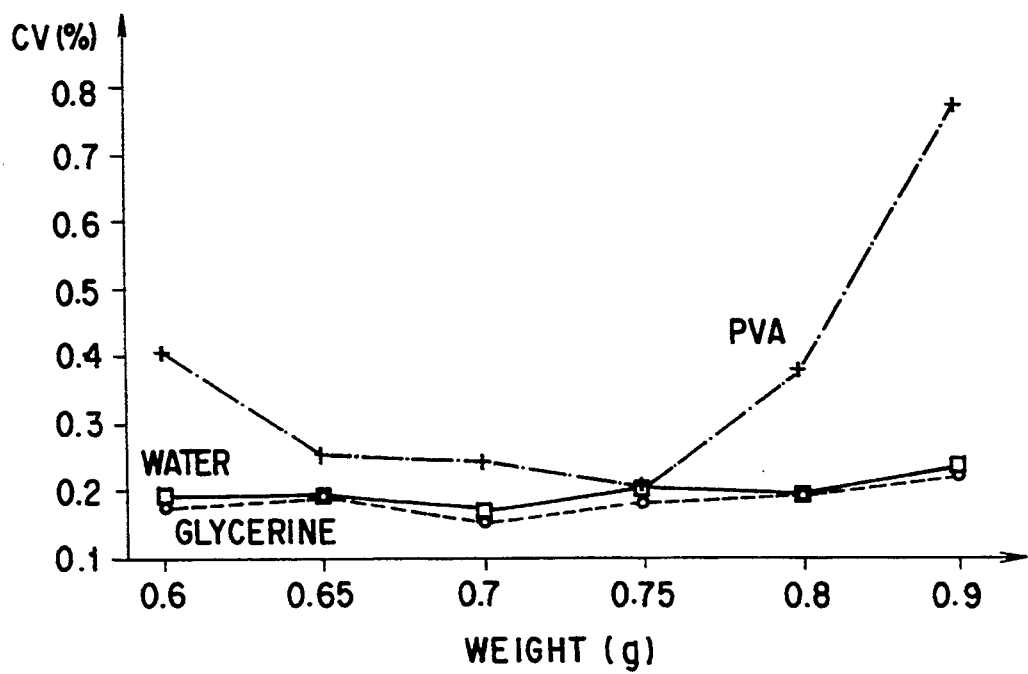
F I G. 21

STIRRING DEVICE

This application is a Continuation of application Ser. No. 07/896,384, filed on Jun. 10, 1992, now abandoned.

BACKGROUND OF THE INVENTION

1. Field of the Invention

The present invention relates to a stirring device for a test of a specimen, which mixes and stirs reaction solutions including reagents and specimens such as serums.

2. Description of the Related Art

In a test of a specimen, when the specimen is reacted with a reagent, it is an indispensable technique in obtaining reaction reproducibility, to stir and homogenize a reaction solution consisting of the specimen and the reagent. High-speed operation of an automatic apparatus (biochemical analyzer) for a test of a specimen has recently been developed, but there is a problem. That is, a predetermined length of time is required for stirring the reaction solution.

An example of a conventional stirring method is a method of stirring a reaction solution by using a motor. FIG. 1 shows an example of this method. A solution in a vessel 10 is stirred by an impeller 12 attached to an end portion of a rotating shaft of a small-sized motor 9.

FIG. 2 shows another example. A freely movable magnet 13 is placed within the vessel 10. A piece of a magnetic metal 9a below the vessel 10 is rotated by the motor 9. By utilizing an attraction force of the magnet 13, the magnet 13 within the vessel 10 is rotated in accordance with the rotation of the piece of a magnetic metal 9a, thereby stirring the solution.

In these methods, stirring is effected in a two-dimensional manner at the bottom part of the vessel 10, and the stirring effect does not act at the upper part of the vessel. Thus, an efficiency of the stirring is low and a long time is required for stirring the entire solution. For example, four seconds or more were required for homogenizing a reaction solution of 400 to 600 μl. A stirring performance CV (coefficient of variance=(standard deviation/average value)×100%) of the stirring device of rotating type as shown in FIGS. 1 and 2 were tested by using a biochemical analyzer for measuring the amount of protein in a serum of 8 μl. The contents of the reaction solution were 308 μl and the number of measurements was 30. The CV was 0.68% for the stirring time of 2 seconds and 0.23% for the stirring time of 4 seconds.

Since the stirring incurs rotation of solution, the solution within the vessel 10 is rotated in a laminar flow, as shown by a broken line in FIGS. 1 and 2, resulting in a longer time for stirring. If the rotation speed of the motor 9 is increased to shorten the stirring time, bubbling occurs, or air (air bubbles) is taken in. Depending on the shape or size of the vessel, solution may spill out of the vessel 10 or be splashed.

An example of a conventional stirring method in which no motor is used is disclosed in U.S. Pat. No. 4,612,291. According to this method, as shown in FIG. 3 (front view) and FIG. 4 (side view), piezoelectric elements 18a and 18b are attached to both surfaces of a metal thin plate 15, thus constituting a bimorph-type piezoelectric vibrator. A distal end portion of the metal thin plate 15 of the piezoelectric vibrator is connected to a stirring rod 14 of a solid structure made of, e.g., stainless steel. A proximal end portion 17 of the metal plate 15 is fixed to a support (not shown). As is shown in FIG. 4, an AC voltage 16 is applied to the piezoelectric elements 18a and 18b, and the piezoelectric elements 18a and 18b are alternately vibrated and the stirring rod 14 is vibrated as shown by broken lines in FIG. 4. By vibration of the stirring rod 14, the solution within the vessel 10 can be stirred. Since the stirring rod 14 is a solid body, the rod 14 as a whole vibrates in a primary mode.

According to this method, since the amplitude of vibration of the stirring member 14 is proportional to the applied voltage, the stirring time can be decreased by increasing the voltage. However, if the amplitude is greatly increased, the stress of the proximal end portion 17 of the piezoelectric vibrator increases, with the result that the piezoelectric vibrator may be damaged or the connecting portion between the metal plate 15 and the stirring rod 14 may be mechanically broken. Since the stirring rod 14 is placed in the vessel with a fixed width, the vessel may be broken by the vibration of the stirring rod if the amplitude of the vibration greatly increases. Thus, the effect of the stirring is limited. In addition, since the vibration mode is the primary mode, the entire reaction solution is not stirred. Thus, the stirring efficiency is low in this method, as with the case of using the motor.

SUMMARY OF THE INVENTION

The present invention has been made in consideration of the above circumstances, and its object is to provide a stirring device capable of homogenizing a reaction solution in a short time.

The stirring device according to the present invention comprises a flexible plate including a main portion and a stirring portion, and a piezoelectric element attached to a surface of the main portion of the flexible plate for vibrating the flexible plate.

According to the present invention, a portion of the flexible plate forming a piezoelectric vibrator with the piezoelectric element is used as a stirring member. Thereby, the vibrator can be vibrated in a higher-order mode, the entire solution can be stirred simultaneously, vertical motion of the solution is caused, and the stirring efficiency can be enhanced.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 7 shows a model of a vibration system of the embodiment of the stirring device according to the present invention;

FIG. 8 shows characteristics of the model shown in FIG. 7, wherein a weight is attached on the surface of a metal thin plate;

FIG. 9 shows characteristics of the model shown in FIG. 7, wherein the weight is not attached;

FIG. 10 shows characteristics of a stirring time in relation to the weight;

FIGS. 11A and 11B show measurement results of the oscillation mode of the embodiment at a given frequency in the air;

FIGS. 12A and 12B show measurement results of the oscillation mode of the embodiment at another frequency in the air;

FIGS. 13A and 13B show measurement results of the oscillation mode of the embodiment at the given frequency in the water;

FIGS. 14A and 14B show measurement results of the oscillation mode of the embodiment at the other frequency in the water;

FIG. 15 is a schematic view of an apparatus for examining frequency characteristics of current in the embodiment;

FIG. 16 is a schematic view of an apparatus for examining frequency characteristics of impedance in the embodiment;

FIG. 20 shows the influence of the stirring time on the stirring performance; and FIG. 21 shows the influence of the weight attached to the piezoelectric vibrator on the stirring performance;

DETAILED DESCRIPTION OF THE PREFERRED EMBODIMENTS

Figure 5:
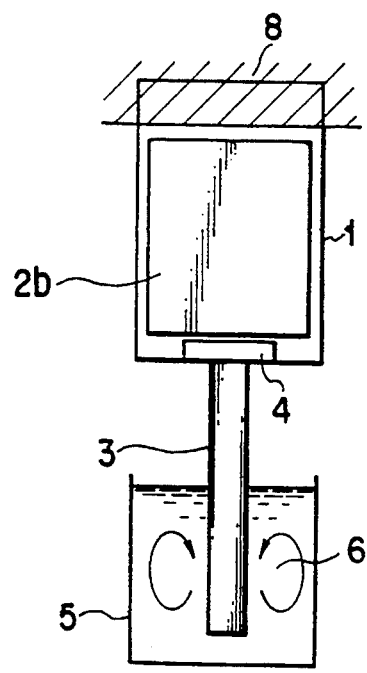
FIG. 5 is a front view of an embodiment of a stirring device according to the present invention.

A preferred embodiment of a stirring device according to the present invention will now be described with reference to the accompanying drawings. FIG. 5 is a front view of the stirring device of a first embodiment, and FIG. 6 is a side view thereof.

Figure 22:
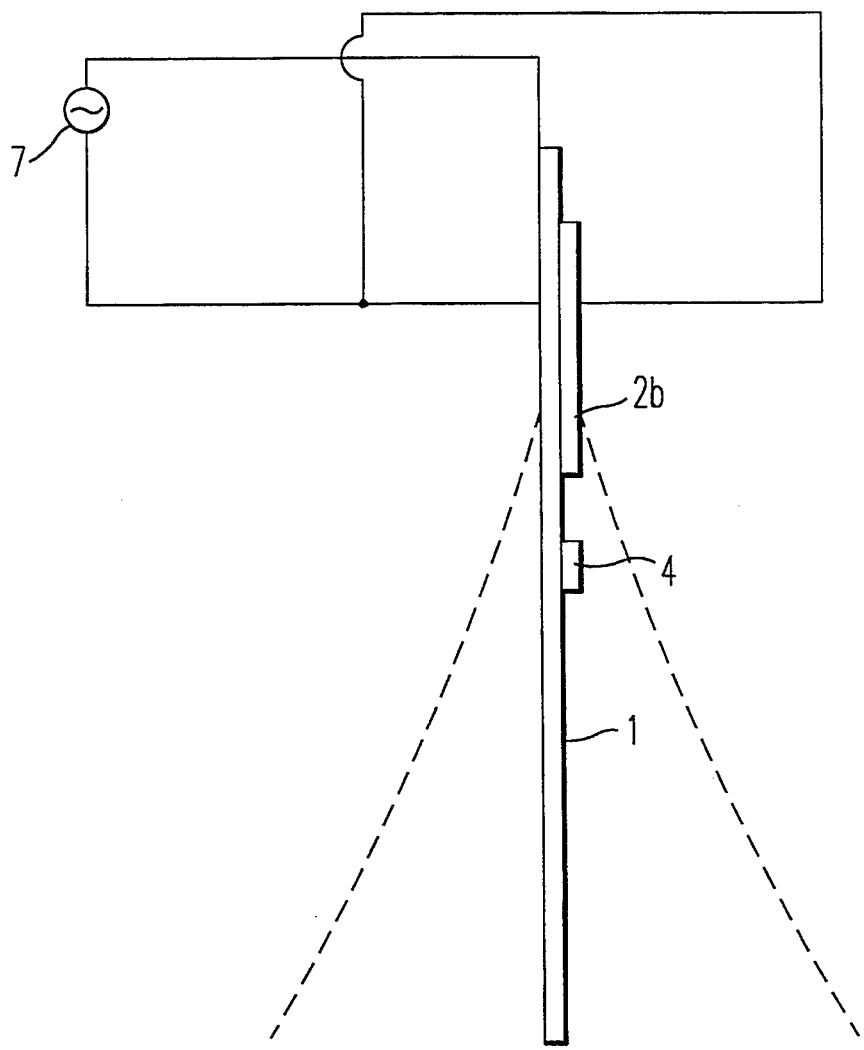
FIG. 22 shows the embodiment according to the present invention where a unimorph piezoelectric element is used to create vibration of the thin plate stirring portion.

Piezoelectric elements 2a and 2b formed of ceramics or the like are attached to both sides of a flexible metal thin plate 1 having a soft structure, thus constituting a bimorph-type piezoelectric vibrator. The piezoelectric element may be attached to only one side of the metal thin plate 1, thus constituting a unimorph-type piezoelectric vibrator, as shown in FIG. 22.

Figure 6:
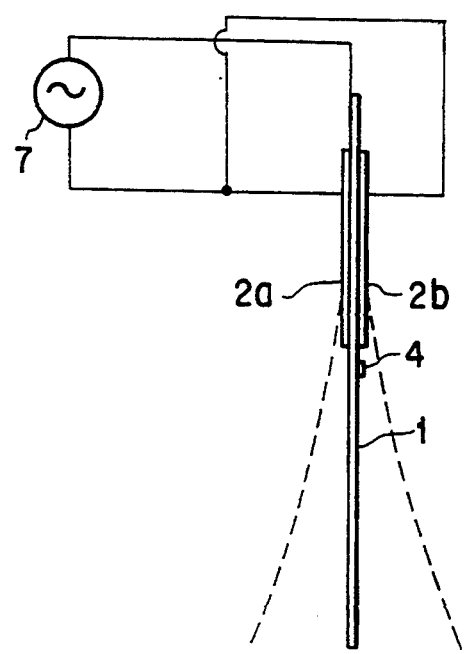
FIG. 6 is a side view of the embodiment shown in FIG. 5.

When an AC voltage is applied from a power supply 7 to the piezoelectric vibrator (piezoelectric elements 2a and 2b), as shown in FIG. 6, the respective piezoelectric elements 2a and 2b extend and contract alternately, and the metal thin plate 1 vibrates in a direction perpendicular to the surface of the plate. A proximal end portion of the plate 1 is fixed to a support 8. In a case of the biochemical analyzer, the support 8 is a stirring device supporting arm attached to a housing of the analyzer.

The distal end portion of the plate 1 extends with the same material having a narrow portion, thus forming a stirring blade 3. The blade 3 is situated within a vessel 5 of a solution as a stirring member. The blade 3 vibrates in accordance with vibration of the piezoelectric vibrator, and the solution within the vessel 5 is stirred by vibration of the blade 3.

A weight 4 capable of adjusting the ratio in mass of the blade portion 3 to the piezoelectric element portion 2a and 2b of the vibrator is attached to the metal thin plate 1 of the piezoelectric vibrator. The weight 4 can be attached to any portion of the plate 1. In this embodiment, for example, as shown in FIG. 5, the weight 4 is attached to a portion adjacent to the proximal end of the blade 3.

Regarding this stirring device, if the amplitude of vibration of the blade 3 is increased, a large bending stress is caused in the piezoelectric elements 2a and 2b. Thus, it is necessary to reduce the stress, while keeping a large amplitude of vibration.

The means for solving this problem will now be explained by using a model. When the model of a stirring device to which the piezoelectric vibrator is applied is converted to a vibration system, this vibration system can be regarded as a forced-vibration system incurring an attenuation of two degrees of freedom, in the case where the equivalent mass and the spring constant of the main portion (piezoelectric elements) of the piezoelectric vibrator are $m_1$ and $k_1$, the equivalent mass and the spring constant of the stirring portion (blade) of the piezoelectric vibrator are $m_2$ and $k_2$, and the solution resistance is c. FIG. 7 shows the model.

When displacements of the vibrator ($m_1$) and blade ($m_2$) from the respective equilibrium states are $x_1$ and $x_2$, and an external force $P_0 \cos\omega t$ is applied from the piezoelectric elements 2a and 2b to the vibrator part ($m_1$), the following motion equations (simultaneous equations) are obtained.

$$\left. \begin{array}{l} m_1\ddot{x}_1 + k_1 x_1 - k_2(x_2 - x_1) - c(\dot{x}_2 - \dot{x}_1) = P_0\cos\omega t \\ m_2\ddot{x}_2 + k_2(x_2 - x_1) + c(\dot{x}_2 - \dot{x}_1) = 0 \end{array} \right\} \quad (1)$$

where mx and kx represent a force, c is a function of speed, and cx also represents a force.

To solve the simultaneous equations, $P_0\cos\omega t$ of the right hand term is changed to the real number part of $P_0\exp(j\omega t)$, i.e., $\text{Re}[P_0\exp(j\omega t)]$. Under the condition that $\dot{x}_1 = j\omega x_1$, $\ddot{x}_1 = -\omega^2 x_1$, $\dot{x}_2 = j\omega x_2$, and $\ddot{x}_2 = j\omega^2 x_2$, the singular solution of the simultaneous equations is obtained. The real number part of the solution is the solution of the simultaneous equations.

Substituting these, the above simultaneous equations are expressed as follows:

$$(-m_1\omega^2 + k_1 + k_2 + j\omega c)x_1 - (k_2 + j\omega c)x_2 = \tag{2}$$
$$Re[P_0\exp(j\omega t)]$$
$$-(k_2 + j\omega c)x_1 + (-m_2\omega^2 + k_2 + j\omega c)x_2 + 0$$

From these simultaneous equations, $x_1$ and $x_2$ will be obtained as follows:

$$x_1 = Re\ [\{((-m_2\omega^2 + k_2) + j\omega c)P_0\exp(j\omega t)\}/\ \{(-m_1\omega^2 + \tag{3}$$
$$k_1)(-m_2\omega^2 + k_2) - m_2 k_2\omega^2 + j\omega c(-m_1\omega^2 + k_1 - m_2\omega^2)\}]$$

$$x_2 = Re\ [\{(k_2 + j\omega c)P_0\exp(j\omega t)\}/\ \{(-m_1\omega^2 + k_1)(-m_2\omega^2 + \tag{4}$$
$$k_2) - m_2 k_2\omega^2 + j\omega c(-m_1\omega^2 + k_1 - m_2\omega^2)\}]$$

To obtain the real number part of this solution, the phase difference $\delta_1$ is defined as follows:

$$\tan\delta_1 = \{\omega c\,(m_2\omega^2 + k_2)^2 + (\omega c)^2\}/\ \{((-m_1\omega^2 + k_1)(-m_2\omega^2 \tag{5}$$
$$+ k_2) - m_2 k_2\omega^2)(-m_2\omega^2 + k_2) + (\omega c)^2\,(-m_1\omega 2 + k_1 - m_2\omega^2)\}$$

Using the phase difference $\delta_1$, $x_1$ is expressed as follows:

$$x_1 = [\{(-m_2\omega^2 + k_2)^2 + (\omega c)^2\}/\{((-m_1\omega^2 + k_1)(-m_2\omega^2 + \tag{6}$$
$$k_2) - m_2 k_2\omega^2)^2 + (\omega c)^2(-m_1\omega^2 + k_1 - m_2\omega_2)^2\}]^{\frac{1}{2}} \times$$
$$P_0\cos(\omega t - \delta_1)$$

The forced displacement $x_1$ of the vibrator (ml) in relation to the displacement $x_{st}$ at the static time is given as follows.

$$x_1/x_{st} = y_1 \cos(\omega t - \delta_1)$$

The following constants are determined. Here, $Y_1$ is the maximum amplitude of vibration in one direction of the vibrator.

$R = m_2/m_1$: the ratio in mass of the blade portion to the piezoelectric element portion of the vibrator
$\omega_0^2 = k_1/m_1$: the inherent circular (angular) vibration frequency (rad/sec)$^2$ of the main vibration system (piezoelectric elements)
$\omega_2 = k_2/m_2$: the inherent circular (angular) vibration frequency (rad/sec)$^2$ of the vibration absorbing system (blade)
$\lambda = \omega_2/\omega_0$: the forced vibration frequency ratio
$\nu = \omega_2/\omega_0$: the inherent vibration frequency ratio
$x_{st} = P_0/k_1$: the static displacement of the main vibration system
$C_c = 2m_2\omega_0$: the critical attenuation coefficient (a value indicating the boundary condition between the aperiodic vibration state and the vibration state of a viscous vibration system)
$\gamma = C/C_c$: the attenuation coefficient ratio
$C = kg.s/cm$ If the $x_1/x_{st}$ is rewritten, the maximum value $y_1$ is found as follows:

$$y_1 = [\{(\nu^2 - \lambda^2)^2 + (2\gamma\lambda)^2\}/\ \{((1 - \lambda^2)(\nu^2 - \lambda^2) - \tag{7}$$
$$R\nu^2\lambda^2)^2 + (2\gamma\lambda)^2(1 - (1 + R)\lambda^2)^2\}]^{\frac{1}{2}}$$

Similarly, the maximum amplitude $y_2$ of vibration in one direction of the blade is given as follows.

$$x_2/x_{st} = y_2 \cos(\omega t - \delta^2)$$

If $\delta_2$ is omitted, the maximum value $y_2$ is as follows:

$$y_2 = [\{\nu^4 + (2\gamma\lambda)^2\}/\ \{((1 - \lambda^2)(\nu^2 - \lambda^2) - \tag{8}$$
$$R\nu^2\lambda^2)^2 + (2\gamma\lambda)^2(1 - (1 + R)\lambda^2)^2\}]^{\frac{1}{2}}$$

FIGS. 8 and 9 show the results of simulation of the maximum values $y_1$ and $y_2$ in relation to an actual angular vibration frequency $\omega(=2\pi f)$, in the case where the attenuation coefficient y of the solution was about 0.1, and the mass ratio R ($=m_2/m_1$) was varied, i.e., the weight 4 attached to the vibrator was varied. FIG. 8 shows the case where R=0.05, and FIG. 9 shows the case where R=1.0.

As is understood from FIGS. 8 and 9, large vibration occurred in the vicinity of the ratio ($\omega/\omega_0$) of the actual angular vibration frequency $\omega$ to the inherent angular vibration frequency $\omega_0$ is 0.9. Although the amplitude of the entire stirring device can be controlled by varying the frequency, it is generally desirable that the voltage is low. It is thus desirable that the driving frequency is made to coincide with the inherent frequency $\omega_0$ of the vibration system having two degrees of freedom, and the stirring device is used in the resonance state. It is therefore preferable that the amplitude takes a maximum value when the vibration frequency ratio $\omega/\omega_0$ is about 0.9.

FIG. 9 shows the state wherein the weight was not used (i.e., $m_1 = m_2$). As is understood from FIG. 9, $y_1$ was substantially equal to $y_2$ and the amplitude of the piezoelectric vibrator must be increased by raising the voltage. The vibration state of the blade 3 indicated by broken lines in FIG. 6 corresponds to the case of FIG. 8.

In this manner, the ratio R in mass of the blade portion to the piezoelectric element portion of the vibrator is varied (specifically, R<1) and the mass $m_1$ of the piezoelectric vibrator or the main vibrating system is made greater than the mass $m_2$ of the blade. Thereby, the amplitude $y_2$ of the blade or the to-be-vibrated system can be made greater than the amplitude $y_1$ of the piezoelectric vibrator or the main vibrating system. The reason for this is that the energy of the main vibrating system can be absorbed by the blade portion (vibration is increased by a vibration-absorbing device) on the basis of the same principle as that of a vibration-absorbing device.

As a result, the amplitude $y_1$ of the piezoelectric vibrator can be made less than the amplitude $y_2$ of the blade, the stirring time ($\approx y_2\omega/2\pi$) can be set in a predetermined period of time, and the amplitude is not increased excessively while contact with the stirring vessel is prevented. Here, the mass ratio R=1 means that the mass of the blade is identical to that of the vibrator.

In the present invention, the piezoelectric vibrator is given a weight, and $m_1$ is made greater than $m_2$, i.e., R<1. Thereby, stirring can be effectively performed, and the amplitude of the piezoelectric vibrator is reduced, thus preventing damage of the piezoelectric element and damage of the metal thin plate of the boundary portion between the piezoelectric vibrator and the blade.

FIG. 10 shows experimental results of the stirring time t (second) in relation to the mass ratio R. As is understood from FIG. 10, more than four seconds were required in the conventional motor system whereas in the present system the stirring time can be reduced to 1.0 to 1.3 seconds by properly setting the mass ratio R. The reason for this is that since the blade 3 is flexible, vibration is performed in the higher-order mode, with the result that disturbance of solution, as indicated by arrows 6 in FIG. 5, occurs in the vessel 5 and the solution within the vessel is totally stirred. Thus, unlike the prior art, air bubbles are not taken in solution, or solution is not spilt over the vessel. Thus, the solution can be homogenized in a short period of time.

FIGS. 11A to 14B show measurement results of the oscillation mode of the stirring device. These show output waveforms (amplitudes) of the piezoelectric vibrator driven by AC 20 V, under the conditions that 600 μl of water was used and a weight of 0.5 g was attached to the bimorph-type piezoelectric vibrator having thickness of 0.2 mm (i.e., R=0.04 to 0.06). The length of the blade was 50 mm.

FIGS. 11A, 12A, 13A, and 14A show the characteristic of an output waveform at the position of the weight, and FIGS. 11B, 12B, 13B, and 14B show the characteristic of an output waveform at the distal end of the blade. FIGS. 11A and 11B show the case where measurement was performed in the air with the driving frequency of 48 Hz, FIGS. 12A and 12B the case where measurement was performed in the air with the driving frequency of 101 Hz, FIGS. 13A and 13B the case where measurement was performed in the water with the frequency of 41 Hz, and FIGS. 14A and 14B the case where measurement was performed in the water with the frequency of 115 Hz. In each state, the amplitude was observed by the naked eyes.

In the case of FIGS. 11A and 11B, the amplitude was 3 mm at the position of the weight and 42 mm at the distal end. In the case of FIGS. 12A and 12B, it was 5 mm at the position of the weight and 11 mm at the distal end. In the case of FIGS. 13A and 13B, it was 0 mm at the position of the weight and 2 mm at the distal end. In the case of FIGS. 14A and 14B, it was 2.5 mm at the position of the weight and 2.5 mm at the distal end. FIGS. 14A and 14B show the case of actual stirring. As is understood from FIGS. 14A and 14B, the period of the vibration at the weight position and that at the distal end position differed from each other so that it can be regarded that the stirring device of the present invention vibrates in the second-order mode.

Next, the frequency characteristics will now be explained. Current was measured by the system shown in FIG. 15, and impedance was measured by the system shown in FIG. 16. In FIG. 15, a vessel 20 contains a solution (600 μl) of 1.5% of PVA (polyvinyl alcohol). A stirring device 22 put in the vessel 20 is connected to a power supply 24. A current value I (mA) at the time the frequency is variable is measured by an oscilloscope 28 via a resistor 26 of 1KΩ. In FIG. 16, similarly, an LCR meter 30 is connected to the stirring device 22, and the impedance Z (KΩ) at the time the frequency is variable is measured.

Figure 17:
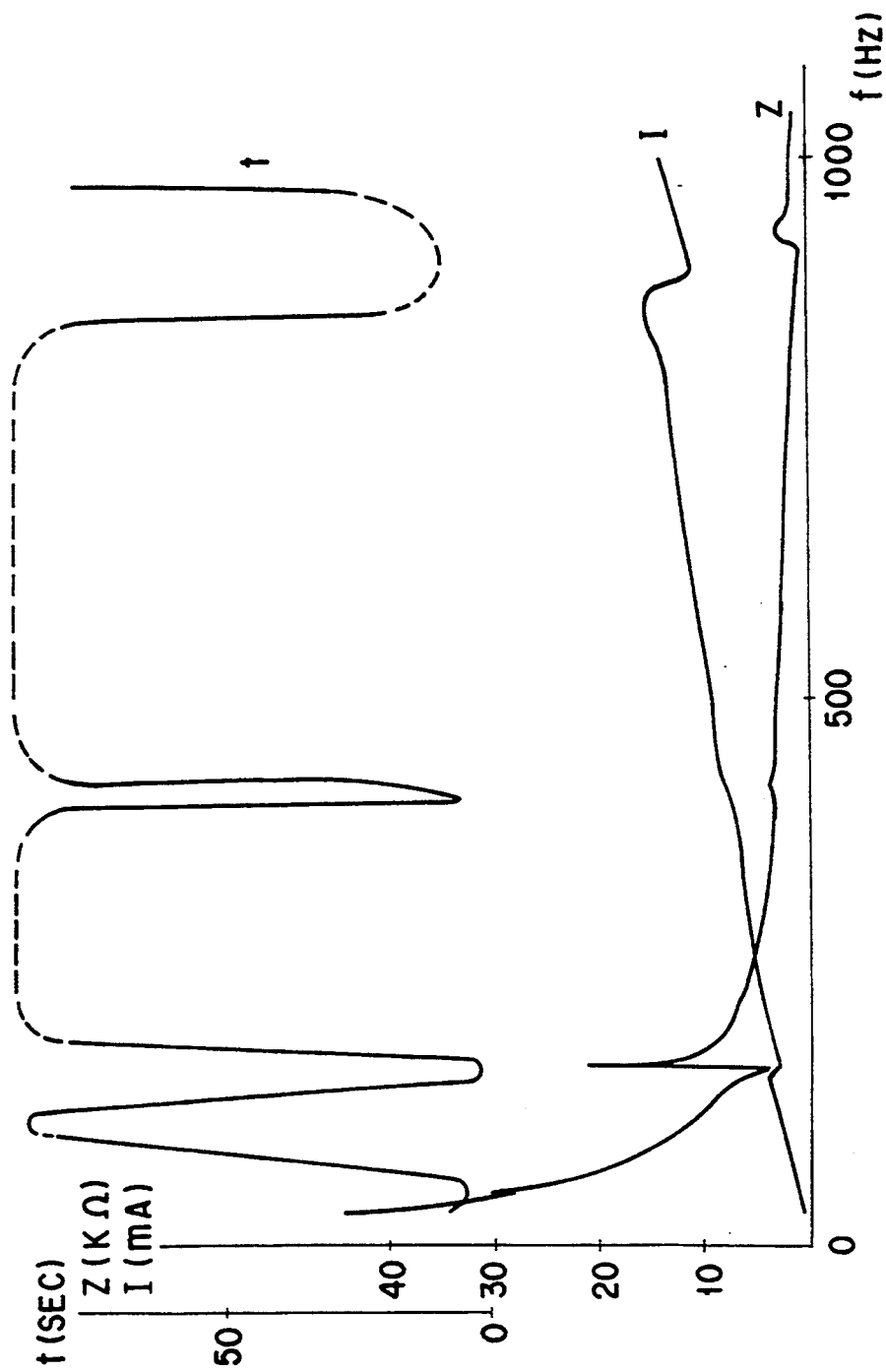
FIG. 17 shows frequency characteristics examined by the apparatuses shown in FIGS. 15 and 16.

The measurement results, as well as stirring time t (second), are shown in FIG. 17. As is understood from FIG. 17, the stirring device of the present system vibrates in the higher-order mode, and stirring can be efficiently performed by using the second-order resonance in the vicinity of frequency 159 Hz. Thus, the driving frequency of the piezoelectric vibrator according to the present invention is set to 159 Hz. Large bubbles were generated and the surface of water was undulated by the third-order resonance in the vicinity of frequency 415 Hz. Small bubbles were generated and bubbling was spread over the surface of water by the fourth-order resonance in the vicinity of frequency 900 HZ.

Lastly, the influence of various parameters on the stirring performance CV (coefficient of variance=(-standard deviation/average value)×100%) will now be explained. It is preferable that the CV has a small value. In this description, a target value of CV is smaller than 0.3%. The following characteristics were measured by the END method, using a piezoelectric element of FEP (tetrafluoroethylene-hexafluoropropylene copolymer) coating 0.25 mm thick and 45 mm long, and a weight of 0.71 g. A 300 ppm orange G aqueous solution was used as a sample. As reagents, water, a 1.5% PVA solution, and a 20% glycerine solution were used.

Figure 18:
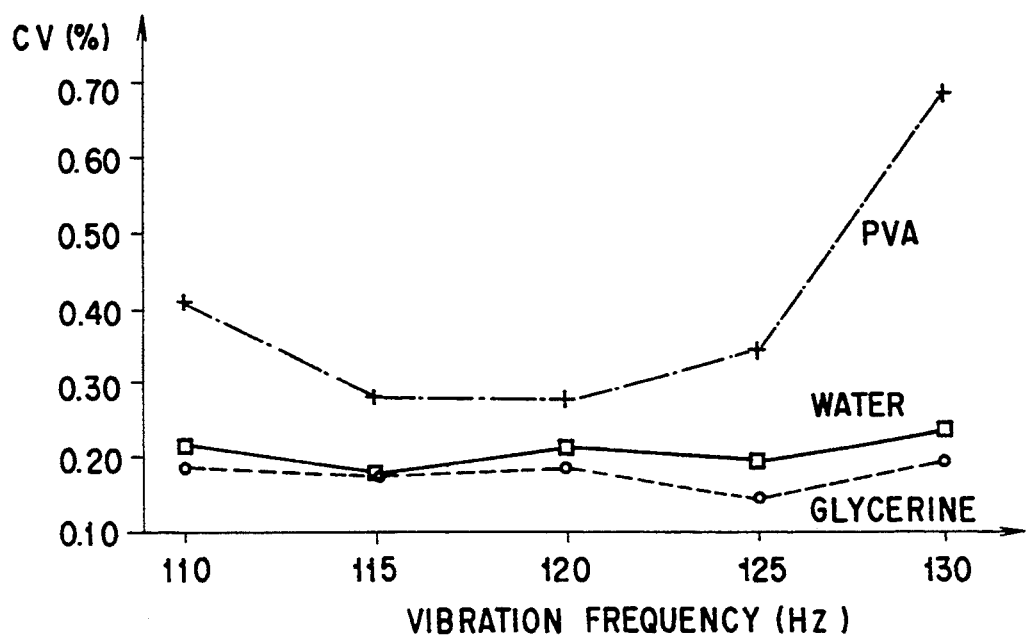
FIG. 18 shows the influence of the vibration frequency on the stirring performance.

FIG. 18 shows the influence of the vibration frequency on the stirring performance. A load voltage was 20.04 V, and a stirring time was 1.9 seconds. As is understood from FIG. 18, when the vibration frequency was 120 Hz, the Cv was low, in particular, in the PVA solution. In the PVA solution, the CV was bad when the vibration frequency was higher or lower than 120 Hz. In water and the glycerine solution, a large variation did not appear in all measurement ranges, and the CV was kept at about 0.20%. That is, the CV was bad when the vibration frequency was low since the effect of stirring was insufficient due to the viscosity of reagent. On the other hand, the CV was lowered when the vibration frequency was high since the reagent was bubbled.

Figure 19:
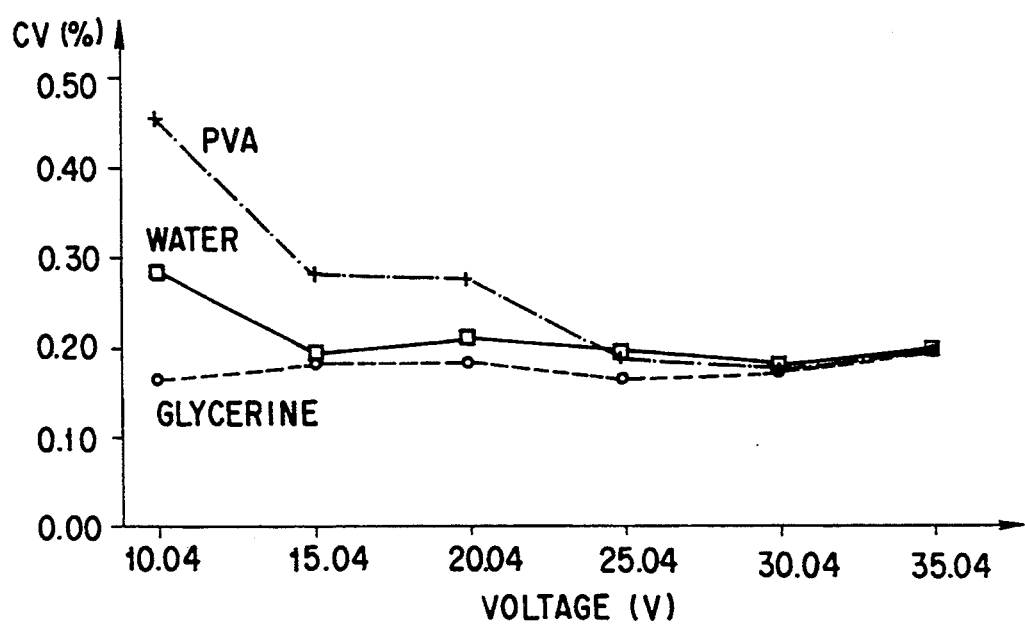
FIG. 19 shows the influence of the load voltage on the stirring performance.

FIG. 19 shows the influence of the load voltage on the stirring performance. The load vibration frequency was 120 Hz, and the stirring time was 1.9 seconds. As is understood from FIG. 19, up to 30 V, as the load voltage increased, the CV substantially decreased in all samples. The CV slightly increased when the load voltage increased to 35 V. If the load voltage is high, the variation of the CV between samples is small.

FIG. 20 shows the influence of the stirring time on the stirring performance. The load frequency was 120 Hz and the load voltage was 20 V. The target value of CV (<0.3%) was attained in all samples by the stirring time of 1.9 seconds. The stirring performance for the PVA solution only increased by increasing the stirring time.

FIG. 21 shows the influence of the weight of the blade on the stirring performance. The load vibration frequency was 120 Hz, the load voltage was 20 V, and the stirring time was 1.9 seconds. A preferable result was obtained using a weight of 0.75 g. The stirring performance for the PVA solution only changed by changing the weight.

Although characteristics are not shown, it is confirmed that since the metal plate 1 was very thin and coated with FEP, the amount of washing water which the stirring device brings from the washing bath into the reaction vessel and the amount of water which stirring device brings out of the reaction vessel, i.e., the amount of carried over were negligible. It is also confirmed that a variation of the CV between individual stirring devices was small.

As has been described above, according to the stirring device of the present embodiment, the piezoelectric vibrator formed of piezoelectric elements attached to the metal thin plate is used, the distal end of the vibrator (metal thin plate) is extended to form the stirring blade, and the weight is attached between the piezoelectric elements and the stirring blade, thereby adjusting the amplitude of vibration of the distal end portion of the stirring blade such that the amplitude of vibration of the distal end portion of the stirring blade is made larger than that of the piezoelectric element. The voltage applied to the piezoelectric element and the frequency of the vibration are adjusted so that the stirring device is vibrated in the higher-order mode. Thereby, at the time of stirring, the entire reaction solution is moved simultaneously, and vertical motion is caused. The entire reaction solution is homogenized in a short time, and precision in analysis is enhanced. Further, since the metal thin plate forms the main portion of the vibrator and the blade portion, the number of connection portions is reduced, and factors of faults are reduced. Therefore, the reliability of the apparatus is increased, and the operator's work load is reduced. The reduction in the number of mechanical parts simplifies the structure of the unit and lowers the cost.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the vibration-generating means is not limited to the piezoelectric element. A voice coil motor or a magnetostrictive element may be used.

The number of the vibration-generating elements attached to each surface of the metal plate is not limited to one. More than two piezoelectric elements, voice coil motors, or magnetostrictive elements may be attached to each surface of the metal plate.

The piezoelectric element can be applicable to both an actuator and a sensor, because of its operational principle. Thus, if a part of the piezoelectric element is used as an actuator and another part is used as a sensor, the driving of piezoelectric element can be controlled in a feedback manner in accordance with the vibration state detected by the sensor. Thereby, stirring can always be performed under optimal conditions in accordance with the quantity of the solution and the variation in viscosity.

Figure 1:
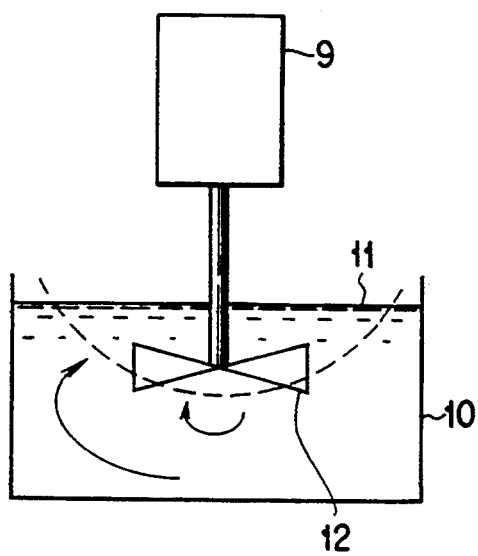
FIG. 1 shows a conventional stirring device using a motor.
Figure 2:
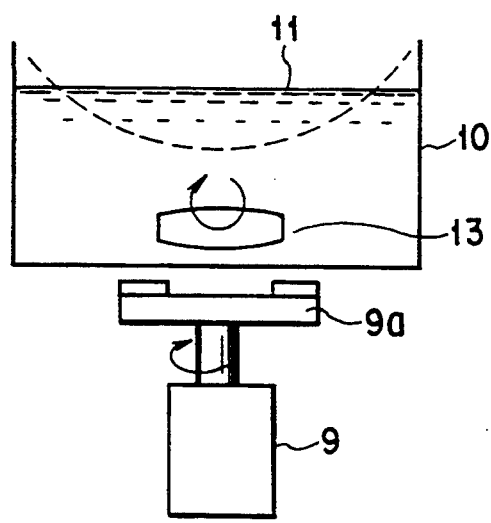
FIG. 2 shows another conventional stirring device using a motor.
Figure 3:
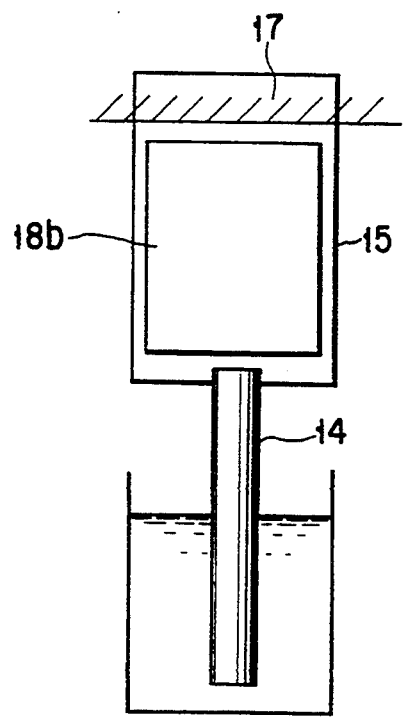
FIG. 3 is a front view showing a conventional stirring device using a piezoelectric element.
Figure 4:
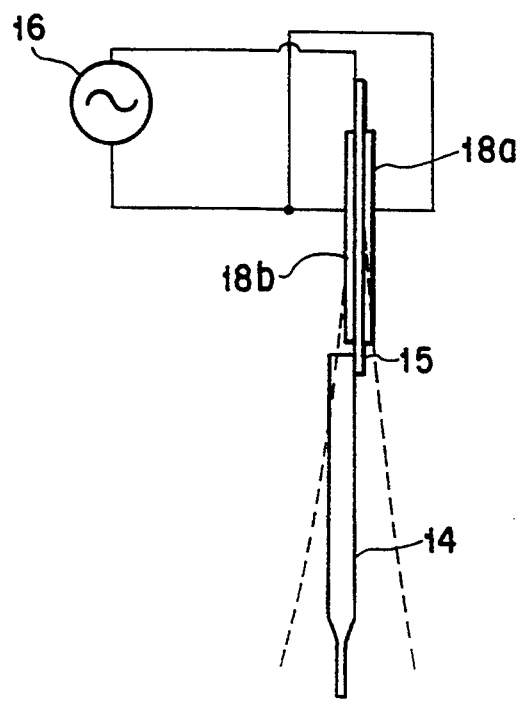
FIG. 4 is a side view of the conventional stirring device shown in FIG. 3.

In the embodiment, the vibrator is vibrated in the lateral direction; however, it may be vibrated in the vertical direction. In this case, the blade may be replaced by a stirring rod having a horizontal plate at its distal end or the impeller as shown in FIG. 1. The degrees of freedom are increased with respect to the position of attachment of the stirring device, without the need to consider the deviation angle of the blade.

Figure 23:
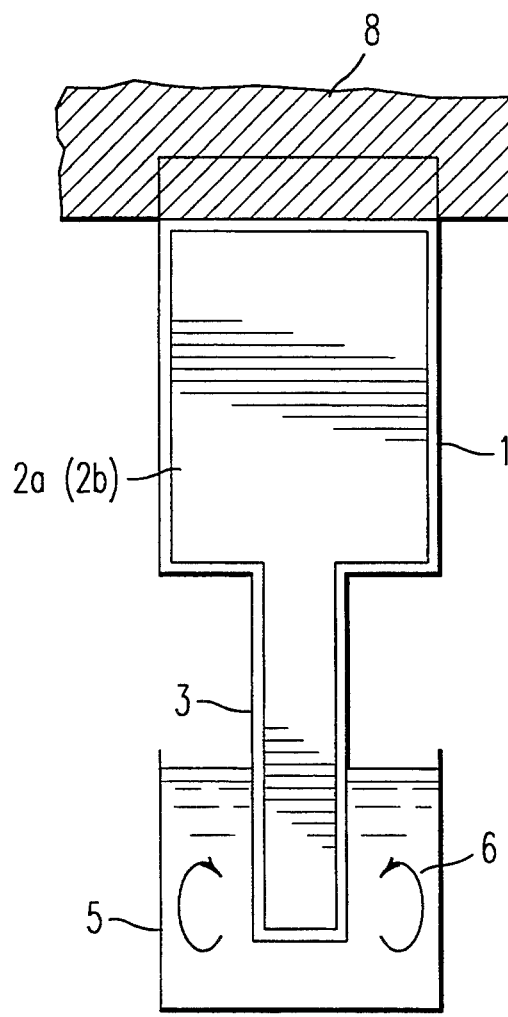
FIG. 23 shows a front view of an embodiment of a stirring device according to the present invention.

In the embodiment, a portion of the metal plate of the vibrator is extended to form the blade; however, the stirring portion may also be formed as part of the piezoelectric vibrator, That is, it is possible to use the piezoelectric vibrator as show in FIG. 23. In an example shown in FIG. 23, a piezoelectric element 2a and/or 2b is attached to an entire surface of the flexible plate 1 of the unimorph-type or bimoroph-type itself as the stirring device.

As has been described above, the present invention can provide a stirring device wherein, since a thin, flexible metal plate is used as material of the stirring member, vibration can be performed in the higher-order mode, the entire reaction solution can be moved simultaneously, and the reaction solution can be moved vertically. Consequently, the reaction solution can be homogenized in a short stirring time, and the treatment of specimen can be performed quickly.

What is claimed is:

1. A stirring device for stirring a solution, comprising:
   a flexible plate constituting a main portion and a stirring portion formed as a single unit; and
   a piezoelectric element attached to a surface of the main portion of said flexible plate for vibrating the stirring portion at a higher order mode defined by any of several higher order modes of a resonant frequency other than a first order, wherein said flexible plate comes into contact with said solution during said stirring of said solution.

2. A stirring device according to claim 1, further comprising a weight which is attached to the flexible plate for changing a mass ratio between the main portion and the stirring portion, the weight acting as a vibration-absorbing device which makes an amplitude of vibration of the stirring portion larger than an amplitude of main portion.

3. A stirring device according to claim 2, wherein the weight has a value for setting the mass ratio of the stirring portion $m_2$ to the main portion $m_1$ ($m_2/m_1$) in a range of 0.04 to 0.06.

4. A stirring device according to claim 2, wherein the weight is attached to a portion of the flexible plate between the stirring portion and the main portion.

5. A stirring device according to claim 1, wherein one piezoelectric element is attached to one surface of the main portion to form a unimorph-type piezoelectric vibrator.

6. A stirring device according to claim 1, wherein two piezoelectric elements are attached to both surfaces of the main portion to form a bimorph-type piezoelectric vibrator.

7. A stirring device according to claim 1, further comprising means for driving the piezoelectric element in a higher-order mode defined by any of several higher orders of a resonant frequency other than a first order.

8. A stirring device according to claim 1, wherein said stirring portion has a width less than a width of said main portion.

9. A stirring device for stirring a solution, comprising:
   a flexible plate constituting a main portion and a stirring portion formed as a single unit; and
   vibration means attached to a surface of the main portion of said flexible plate for vibrating the stirring portion at a higher order mode defined by any of several higher modes of a resonant frequency other than a first order, wherein said flexible plate comes into contact with said solution during said stirring of said solution.

10. A stirring device according to claim 9, further comprising a weight which is attached to the flexible plate for changing a mass ratio between the main portion and the stirring portion, the weight acting as a vibration-absorbing device which makes an amplitude of vibration of the stirring portion larger than an amplitude of main portion.

11. A stirring device according to claim 10, wherein the weight has a value for setting the mass ratio of the stirring portion $m_2$ to the main portion $m_1(m_2/m_1)$ in a range of 0.04 to 0.06.

12. A stirring device according to claim 10, wherein the weight is attached to a portion of the flexible plate between the stirring portion and the main portion.

13. A stirring device according to claim 9, wherein said vibration means comprises a piezoelectric element which is attached to one surface of the main portion, the piezoelectric element forming a unimorph-type piezoelectric vibrator.

14. A stirring device according to claim 9, wherein said vibration means comprises two piezoelectric elements which are attached to both surfaces of the main portion, the two piezoelectric elements forming a bimorph-type piezoelectric vibrator.

15. A stirring device according to claim 9, further comprising means for driving the vibration element in a higher-order mode defined by any of several higher orders of a resonant frequency other than a first order.

16. A stirring device according to claim 9, wherein said stirring portion has a width less than a width of said main portion.

17. A stirring device comprising:
a flexible plate having one end portion to be positioned in a vessel for a solution to be stirred and the other end portion fixed over the vessel; and
a piezoelectric element attached to a surface of the other end portion of said flexible plate for vibrating the one end portion of said flexible plate at a higher order mode defined by any of several higher modes of a resonant frequency other than a first order, wherein said flexible plate comes into contact with said solution during said stirring of said solution.

18. A stirring device according to claim 17, wherein said piezoelectric element is attached to an entire surface of said flexible plate.

19. A stirring device according to claim 17, wherein said said one end portion has a width narrower than a width of said other end portion, wherein said other end portion width includes said piezoelectric element.

20. A stirring apparatus comprising:
a stirring plate being flexible and constituting a single unit having a portion extendable into an aqueous solution for stirring said aqueous solution and having first and second major surfaces opposed one another;
a first piezoelectric element formed on said first major surface of the stirring plate in an area away from the portion extendable in the aqueous solution;
a second piezoelectric element formed on said second major surface of the stirring plate in an area away from the portion extendable in the aqueous solution; and
wherein, said first and second piezoelectric elements sandwich the stirring plate and swing the stirring plate when alternately charged by an operating means which drives the stirring plate at a higher order mode defined by any of several higher order modes of a resonant frequency other than a first order between to discreet maximum positions generating a bimorphic-type piezoelectric vibrator.

21. The stirring apparatus of claim 20, further comprising:
a weight mounted on the first major surface of the stirring plate in an area where the first and second piezoelectric elements do not contact the stirring plate; and
wherein, said weight may be mounted along any portion of the stirring plate to adjust an amplitude between said discreet maximum positions of the stirring plate.

22. The stirring apparatus of claim 21, wherein the amplitude of the discreet maximum positions of the stirring plate is set to a maximum value defined by physical limitations of the stirring apparatus when in operation and the vibration frequency ratio $\omega_o/\omega$ is greater or equal to 0.9, where $\omega_o$ is the inherent angular vibration frequency and $\omega$ is the actual angular vibration frequency.

* * * * *